US009642659B2

(12) United States Patent
Velikov et al.

(10) Patent No.: US 9,642,659 B2
(45) Date of Patent: May 9, 2017

(54) IMPLANTABLE INSERT SLEEVE

(71) Applicant: ZIMMER GmbH, Winterthur (CH)

(72) Inventors: Jordan Velikov, Horgen (CH); Thomas Teschke, Ruggel (LI)

(73) Assignee: Zimmer GMBH, Winterthur (CH)

( * ) Notice: Subject to any disclaimer, the term of this patent is extended or adjusted under 35 U.S.C. 154(b) by 0 days.

(21) Appl. No.: 14/783,598

(22) PCT Filed: Apr. 11, 2014

(86) PCT No.: PCT/EP2014/057434
§ 371 (c)(1),
(2) Date: Oct. 9, 2015

(87) PCT Pub. No.: WO2014/167117
PCT Pub. Date: Oct. 16, 2014

(65) Prior Publication Data
US 2016/0081729 A1   Mar. 24, 2016

(30) Foreign Application Priority Data
Apr. 12, 2013   (EP) ..................................... 13163522

(51) Int. Cl.
*A61B 17/80* (2006.01)
*A61B 17/86* (2006.01)
*A61B 17/00* (2006.01)

(52) U.S. Cl.
CPC ...... *A61B 17/8047* (2013.01); *A61B 17/8695* (2013.01); *A61B 2017/00004* (2013.01); *A61B 2017/00946* (2013.01)

(58) Field of Classification Search
CPC ....................... A61B 17/8047; A61B 17/8085
See application file for complete search history.

(56) References Cited

U.S. PATENT DOCUMENTS

| | | | |
|---|---|---|---|
| 2001/0014807 | A1 | 8/2001 | Wagner et al. |
| 2004/0220570 | A1 | 11/2004 | Frigg |
| 2011/0319942 | A1 | 12/2011 | Bottlang et al. |
| 2012/0016365 | A1 | 1/2012 | Freid |

(Continued)

OTHER PUBLICATIONS

"European Application Serial No. 131635229, Extended European Search Report mailed Sep. 20, 2013", 7 pgs.

(Continued)

*Primary Examiner* — David Bates
*Assistant Examiner* — Olivia C Chang
(74) *Attorney, Agent, or Firm* — Schwegman Lundberg & Woessner, P.A.

(57) ABSTRACT

The present disclosure relates to an insert sleeve (19) designed for being inserted into a through hole (17) of an implant (11), comprising a body (21) with a through hole (23) defining an axial direction (29) for receiving a bone anchoring element (25), in particular a bone screw, said body (21) being made of a material having a first modulus of elasticity and including multiple recesses (27) arranged in circumferential direction around said through hole (23) of said insert sleeve (19) for reducing a stiffness of said insert sleeve (19) in a direction transverse (31, 33) to said axial direction (29). At least one of said recesses (27) is filled with a filler material (41) having a second modulus of elasticity different from said first modulus of elasticity.

18 Claims, 3 Drawing Sheets

(56) References Cited

U.S. PATENT DOCUMENTS

2012/0303071 A1 11/2012 Black et al.
2012/0310289 A1* 12/2012 Bottlang ............ A61B 17/8004
            606/291

OTHER PUBLICATIONS

"International Application Serial No. PCT/EP2014/057434, International Preliminary Report on Patentability mailed Oct. 13, 2015", 5 pgs.
"International Application Serial No. PCT/EP2014/057434, International Search Report mailed May 13, 2014", 4 pgs.
"International Application Serial No. PCT/EP2014/057434, Written Opinion mailed May 13, 2014", 4 pgs.

* cited by examiner a)

b)

IMPLANTABLE INSERT SLEEVE

This application is a U.S. National Stage Application under 35 U.S.C. 371 from International Application Serial No. PCT/EP2014/057434, filed on Apr. 11, 2014, and published as WO 2014/167117 A1 on Oct. 16, 2014, which claims priority to European Application No. 13163522.9, filed on Apr. 12, 2013, the benefit of priority of each of which is claimed hereby, and each of which are incorporated by reference herein in its entirety.

BACKGROUND

The present disclosure relates to orthopedic implants, and more particularly, to insert sleeves designed for being inserted into a through hole of an implant.

For the treatment of a bone fracture such as a fracture of the proximal humerus the fracture may be fixed by means of pins, screws, wires or plates after alignment of the individual bone fragments in their correct positions (repositioning). In particular, an osteosynthetic plate can be used which is fastened to the individual bone fragments by means of screws to hold the individual bone fragments in a fixed position with respect to one another.

According to Wolff's law and stress shielding theory, decreasing the loading on the bone, e.g. by means of an osteosynthetic plate, leads to weakening of the bone. Attempts have been made to develop osteosynthetic plates that are less rigid.

SUMMARY

The present disclosure provides an insert sleeve designed for being inserted into a through hole of an implant. The insert sleeve comprises a body with a through hole defining an axial direction for receiving a bone anchoring element, in particular a bone screw. The body is made of a material having a first modulus of elasticity and includes multiple recesses arranged in circumferential direction around the through hole of the insert sleeve in particular for reducing a transverse stiffness of the insert sleeve and/or of the implant, in particular as compared to a same body without such multiple recesses and/or a same implant without such multiple recesses in a same body.

It has been found that such insert sleeves, when inserted in through holes of an implant attached to a bone, reduce the transverse stiffness of the implant and, thus, aid in stimulating remodeling of the bone. The transverse stiffness is a stiffness in a direction transverse, in particular at least essentially perpendicular, in particular perpendicular, to the axial direction of the through hole of the insert sleeve. In particular, the multiple recesses are configured and arranged to increase the flexibility of the insert sleeve.

In an aspect, the recesses are arranged and/or shaped such that the transverse stiffness is lower in a first transverse direction than in a second transverse direction. Thus, the transverse stiffness of the insert sleeve may be directional-dependent. The first transverse direction and the second transverse direction form a transverse plane, i.e. a plane transverse to the axial direction of the through hole of the insert sleeve. The first and second transverse directions may be perpendicular to each other. The insert sleeve may be inserted into a through hole of an elongate implant such that the first transverse direction coincides with a longitudinal axis of the elongate implant.

In another aspect, at least one of the recesses is filled with a filler material having a second modulus of elasticity different from the first modulus of elasticity. In particular, the second modulus of elasticity may be smaller than the first modulus of elasticity.

In another aspect, the filler material is bioresorbable. The filler material can be broken down by the body, i.e. will gradually resorb and be cleared from the body. Thus, the transverse stiffness of the insert sleeve may be time-dependent, in particular decrease over time. Consequently, more and more load initially borne by the implant may be transferred to the bone.

In another aspect, the recesses open out to at least one axial and/or annual face of the insert sleeve. In another aspect, at least one of the recesses completely penetrates the body in axial direction, i.e. forms athrough passage.

In another aspect, the insert sleeve is a circular cylinder. Alternatively, the insert sleeve may have oval or rectangular shape. The insert sleeve may have an inner annular surface and/or an outer annular surface.

In another aspect, the recesses are arranged and/or shaped symmetrically with respect to a plane defined by the axial direction and the first transverse direction and/or with respect to a plane defined by the axial direction and the second transverse direction.

In another aspect, at least one of the recesses is of oblong curved shape extending in circumferential direction, and/or least one of the recesses is a slit extending in radial direction.

In another aspect, at a proximal side of the insert sleeve, a diameter of the through hole of the insert sleeve is enlarged to form an impression for receiving a head of the bone anchoring element. The proximal side of the insert sleeve is that side of the insert sleeve that faces the surgeon during surgery. The bone anchoring element is inserted from proximal to distal into the through hole of the insert sleeve. In implanted state, the head of the bone anchoring device points in proximal direction.

In another aspect, the insert sleeve is configured such that at least part of a shaft of the bone anchoring element is feedable through the through hole of the insert sleeve, whereas a head of the bone anchoring element is receivable in an impression formed at a proximal side of the insert sleeve.

In yet another aspect, the insert sleeve is configured such that the bone anchoring element is uniaxially receivable in the insert sleeve and/or such the said insert sleeve is uniaxially receivable in the through hole of the implant.

In still another aspect, the insert sleeve is provided with a bushing at an inner annular surface of the body. The bushing may be made of a material yielding better tribological properties than the material of the body when in contact with the bone anchoring element. In an aspect, the insert sleeve comprises at least one feature providing a security against rotation relative to the axial direction when inserted in the trough hole of the implant. This prevents the insert sleeve from rotating. The at least one feature providing a security against rotation could be a rib, a web, a projection or the like which extends away from the insert sleeve and engages a counter-shaped feature such as a groove provided at the through hole of the implant. The arrangement of projection and groove could also be vice versa or a multiple of these arrangements could be provided, in particular in an alternating manner. In another aspect, the insert sleeve comprises at least one guide feature configured such that the insert sleeve may be received in the trough hole of the implant only in at least one pre-defined discrete rotational orientation relative to the axial direction, in particular in multiple pre-defined discrete rotational orientations. This means that the insert can only be positioned in the implant in (a) pre-selected orientation(s). This is in particular used when the stiffness of the sleeve changes for different transverse directions. The at least one feature providing a security against rotation and the at least one guide feature could be one and the same. In a further aspect, the insert sleeve comprises at least one axial stop that is configured to provide an abutment when inserting the insert sleeve in the through hole of the implant. This results in a defined axial position of the insert sleeve within the implant. The axial stop could for example be formed by a particular shape of the insert sleeve cooperating with a counter-shaped through hole of the implant such as a snap-fit connection or a conical shaping of the insert sleeve.

The present disclosure further relates to a set of insert sleeves in accordance with the above description, wherein groups of insert sleeves differ from each other in arrangement and/or shape of the recesses, wherein insert sleeves within a group are alike.

The present disclosure further relates to an implant system comprising an implant, in particular a bone fixing apparatus such as an orthopedic plate, including multiple through holes, in particular bores, and at least one insert sleeve in accordance with the above description, in particular designed for being inserted into one of said through holes. Optionally, the implant system may also comprise multiple bone anchoring elements. In particular, the at least one insert sleeve is arranged in one of the through holes of the implant, in particular is configured to be uniaxially received in one of the through holes of the implant. In particular, the at least one insert sleeve comprises multiple insert sleeves, in particular comprises one insert sleeve for each of the through holes.

It will be appreciated that the specific features of the embodiments described above can be combined. Thus any combinations of the features described in the dependent claims are disclosed herein, be they explicitly mentioned or not.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein:

FIG. 2a is a perspective view of insert sleeves inserted into through holes of an osteosynthetic plate according to another exemplary embodiment of the present disclosure.

FIG. 2b is a top view of the osteosynthetic plate of FIG. 2a.

FIG. 2c is a cross-sectional view of the osteosynthetic plate of FIG. 2b along Line A-A.

FIG. 2d is a cross-sectional view of the osteosynthetic plate of FIG. 2b along Line B-B.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
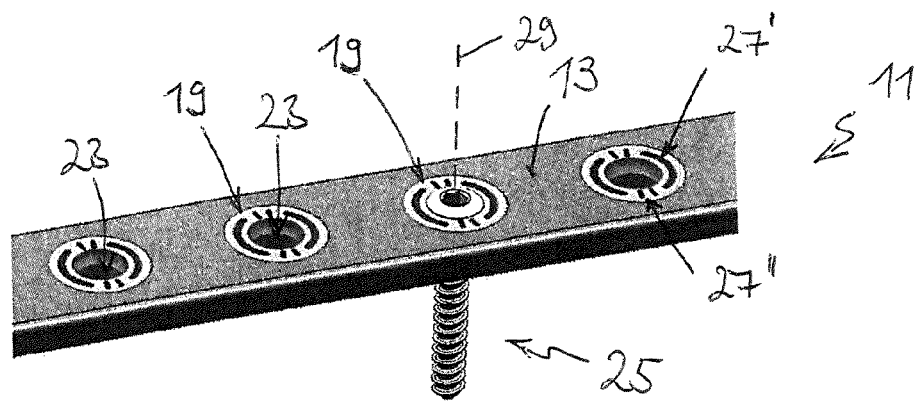
FIG. 1 is a perspective view of insert sleeves inserted into through holes of an osteosynthetic plate according to one exemplary embodiment of the present disclosure.
Figure 2:
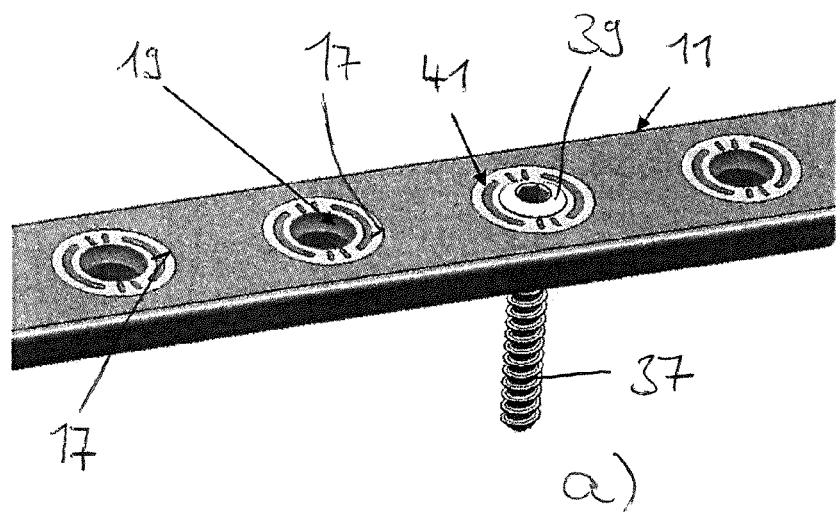
Figure 2:
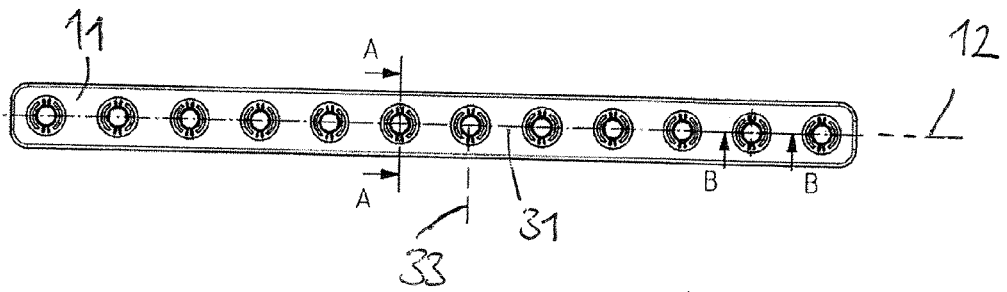
Figure 2:
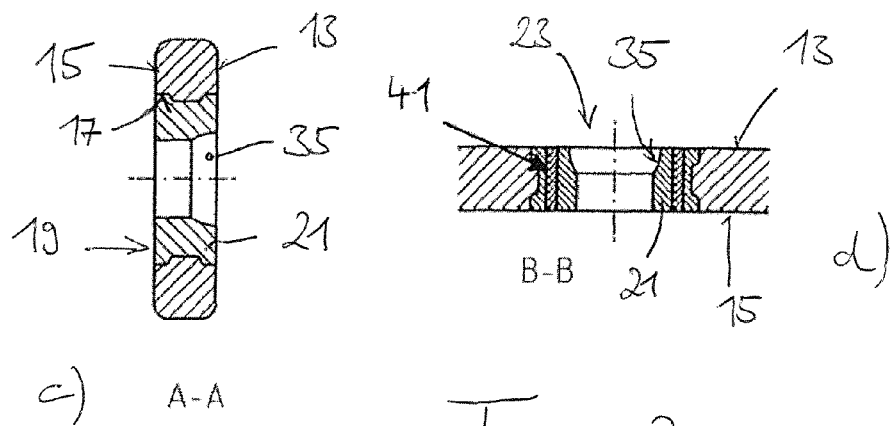

Referring to FIG. 1, osteosynthetic plate 11 is shown and forms an elongate body including proximal side 13 and distal side 15 (cf. FIGS. 2c, 2d). The osteosynthetic plate 11 may be used in treatment of bone fractures, for example. The osteosynthetic plate 11 includes multiple through holes 17 arranged in row along a longitudinal axis 12 of the elongate osteosynthetic plate 11 (cf. FIG. 2b) to hold bone screws 25 for fastening the osteosynthetic plate 11 to the bone or bone fractures, respectively.

Insert sleeves 19 are inserted into the through holes 17. The insert sleeves 19 may be made of a plastic material such as a polymer or an alloy, for example. Each of the insert sleeves 19 is formed as a circular cylinder and is mainly comprised of a body 21 (cf. FIGS. 2c, 2d) that includes a central through hole 23 for uniaxially receiving the bone screw 25 as well as multiple recesses 27 or cut-outs arranged in circular manner around the central through hole 23 that defines an axial direction 29. The axial direction 29 is common to through hole 23 of the insert sleeve 19, through hole 17 of the osteosynthetic plate 11, and bone screw 25. Each of the recesses 27 completely penetrates the body 21 all the way from the proximal side 13 to the distal side 15 and is confined between radially inner and outer portions of the body 21.

The multiple recesses 27 of each insert sleeve 19 comprise two elongated curved recesses 27' arranged opposite to each other with respect to the axial direction 29 and along a first transverse direction 31 (cf. FIG. 2b), and two pairs of radially extending recesses 27" arranged opposite to each other along a second transverse direction 33 (cf. FIG. 2b) perpendicular to the first transverse direction 31. The first and second directions 31, 33 form a plane transverse to the axial direction 29 of the insert sleeve 19. By omitting material from the body 21 to form the recesses 27 the in-plane stiffness of the insert sleeve 19 is reduced. In particular, the transverse stiffness is lower in the first transverse direction 31 than in the second transverse direction 33 due to the arrangement and the shape of the recesses 27. At least one (not-shown) guide feature providing also a security against rotation relative to the axial direction 29 can be included in the insert sleeve 19 in order to ensure that a correct positioning of the insert sleeve 19 within the through hole 17 of the implant 11 is brought about. Thus, the first transverse direction 31 of the insert sleeve 19 can be selected in parallel to the longitudinal axis 12 of the implant 11.

The reduced stiffness of the insert sleeves 19 leads to a corresponding reduced stiffness of the osteosynthetic plate 11 and osteosynthetic plate system, respectively. Thus, the present osteosynthetic plate system beneficially assists in stimulating the bone to remodel itself over time.

Referring to FIG. 2a, each of the recesses 27 of each insert sleeve 19 is fully filled with a filler material 41. The filler material may be made of a polymer such as polyether ether ketone (PEEK), for example. The filler material 41 has a modulus of elasticity which is smaller than the modulus of elasticity of the body 21 but may in general also be higher. The transverse stiffness of the insert sleeve 19 according to FIG. 2a is higher than the transverse stiffness of the insert sleeve 19 according to FIG. 1. In a particular embodiment, the filler material 41 is bioresorbable. This results in a change of the transverse stiffness of the insert sleeve 19 over time. In particular, the transverse stiffness decreases. Thus, the load that has to be borne by the bone increases over time to further stimulate the bone to remodel itself.

As can be seen in FIGS. 2c and 2d, the insert sleeve 19 is pressed into the through hole 17 of the osteosynthetic plate 11 to form a snap-fit connection. In general, the insert sleeves 19 may also be threadable into the through holes 17 of the osteosynthetic plate 11.

A diameter of the through hole 23 of each insert sleeve 19 is larger in a proximal section of the insert sleeve 19 than in a distal section to form an impression 35. The diameter of the through hole 23 is such that a shaft 37 (cf. FIG. 2a) of the bone screw 25 may pass even through the smaller distal part of the through hole 23 whereas a head 39 (cf. FIG. 2a) of the bone screw 25 may not pass through the smaller distal part of the through hole 23 and is seatably received in the impression 35.

Figure 3:
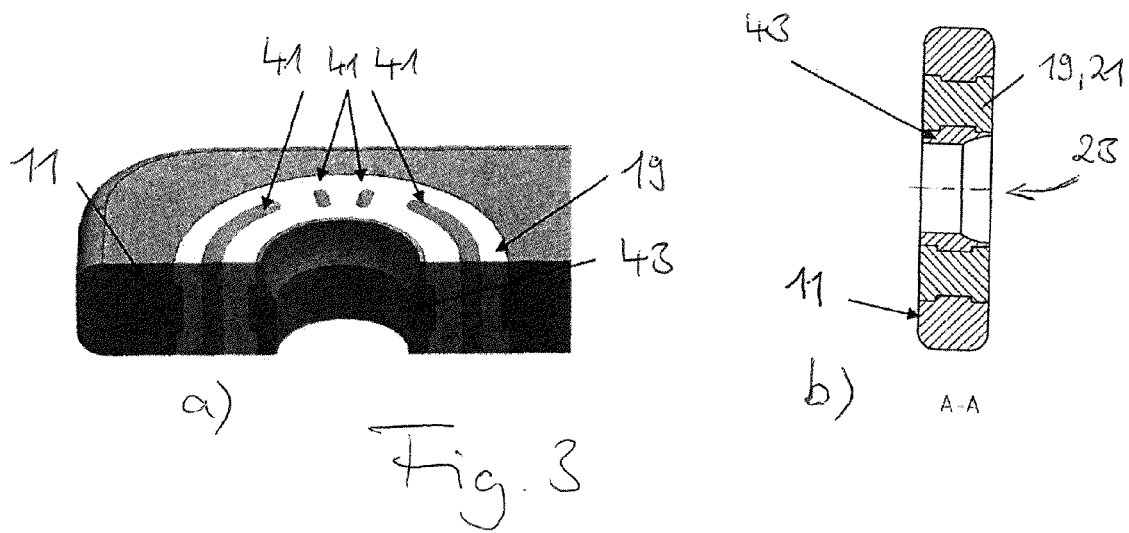
FIG. 3a is a fragmentary view of an insert sleeve inserted into a through hole of an osteosynthetic plate according to another exemplary embodiment of the present disclosure.
FIG. 3b is a cross-sectional view of the osteosynthetic plate of FIG. 3a similar to FIG. 2c.

Referring to FIGS. 3a and 3b, the body 21 of each insert sleeve 19 is provided with a bushing 43 at its inner annular surface, wherein the bushing 43 forms the through hole 23 of the insert sleeve 19. The bushing 43 may be provided to improve the tribological properties of the interface between the respective bone screw 25 and the respective insert sleeve 19.

Figure 4:
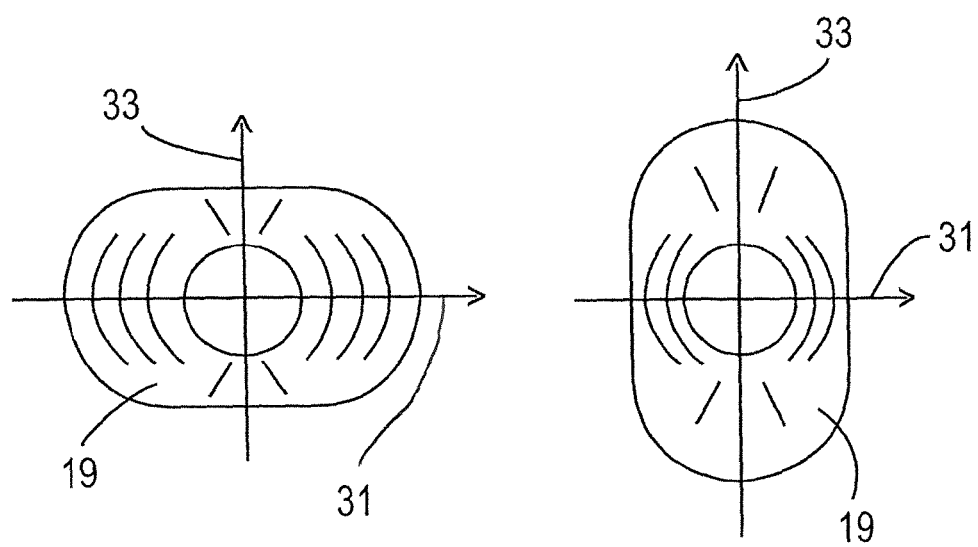
FIG. 4 shows top views of two insert sleeves according to other exemplary embodiments of the present disclosure.

The insert sleeves 19 may have a shape or an outer shape, respectively, which differs from a circular cylinder. As shown in FIG. 4, the insert sleeves 19 may also have an oval shape, for example, wherein the long axis of the oval may either coincide with the first transverse direction 31 (left drawing) or the second transverse direction 33 (right drawing).

While the prosthesis design shown and described above is an osteosynthetic plate system, it is contemplated that other implants such as acetabular cups in hip replacements or vertebral plates may also be made in accordance with the present disclosure.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

REFERENCE NUMERAL LIST 11 osteosynthetic plate
12 longitudinal axis
13 proximal side
15 distal side
17 through holes
19 insert sleeve
21 body
23 through hole
25 bone screw
27 recess
29 axial direction
31 first transverse direction
33 second transverse direction
35 impression
37 shaft
39 head
41 filler material
43 bushing

The invention claimed is:

1. An insert sleeve designed for being inserted into a through hole of an implant, said insert sleeve comprising a body with a through hole defining an axial direction for receiving a bone anchoring element, in particular a bone screw, said body being made of a material having a first modulus of elasticity and including multiple recesses arranged in circumferential direction around said through hole of said insert sleeve for reducing a stiffness of said insert sleeve in a direction transverse to said axial direction, wherein at least one of said recesses is filled with a filler material having a second modulus of elasticity different from said first modulus of elasticity, and wherein the filler material is bioresorbable.

2. The insert sleeve in accordance with claim 1, wherein said multiple recesses are configured and arranged to increase the flexibility of said insert sleeve.

3. The insert sleeve in accordance with claim 1, wherein said recesses are arranged and/or shaped such that said transverse stiffness is lower in a first transverse direction than in a second transverse direction.

4. The insert sleeve in accordance with claim 1, wherein, said second modulus of elasticity is smaller than said first modulus of elasticity.

5. The insert sleeve in accordance with claim 1, wherein, said recesses open out to at least one axial and/or annular face of said insert sleeve.

6. The insert sleeve in accordance with claim 1, wherein at least one of said recesses completely penetrates said body in axial direction.

7. The insert sleeve in accordance with claim 1, wherein said insert sleeve is a circular cylinder.

8. The insert sleeve in accordance with claim 1, wherein said recesses are arranged and/or shaped symmetrically with respect to a plane defined by said axial direction and said first transverse direction and/or with respect to a plane defined by said axial direction and said second transverse direction.

9. The insert sleeve in accordance with claim 1, wherein at least one of said recesses is a slit extending in radial direction.

10. The insert sleeve in accordance with claim 1, wherein, at a proximal side of said insert sleeve, a diameter of said through hole of said insert sleeve is enlarged to form an impression for receiving a head of said bone anchoring element.

11. The insert sleeve in accordance with claim 1, wherein said insert sleeve is configured such that at least part of a shaft of said bone anchoring element is feedable through said through hole of said insert sleeve , whereas a head of said bone anchoring element is receivable in an impression formed at a proximal side of said insert sleeve.

12. The insert sleeve in accordance with claim 1, wherein said insert sleeve is configured such that said bone anchoring element is uniaxially receivable in said insert sleeve and/or such that said insert sleeve is uniaxially receivable in said through hole of said implant.

13. The insert sleeve in accordance with claim 1, wherein said insert sleeve is provided with a bushing at an inner annular surface of said body.

14. The insert sleeve in accordance with claim 1, wherein said insert sleeve comprises at least one feature providing a security against rotation relative to said axial direction when inserted in said through hole of said implant.

15. The insert sleeve in accordance with claim 1, wherein said insert sleeve comprises at least one guide feature configured such that said insert sleeve may be received in said through hole of said implant only in at least one pre-defined discrete rotational orientation relative to said axial direction, in particular in multiple pre-defined discrete rotational orientations.

16. The insert sleeve in accordance with claim 1, wherein said insert sleeve comprises at least one axial stop that is configured to provide an abutment when inserting said insert sleeve in said through hole of said implant.

17. The insert sleeve in accordance with claim 1, in combination with an implant, wherein the insert sleeve is pressed into a through hole of the implant to form a snap-fit connection.

18. The insert sleeve in accordance with claim 1, in combination with an implant, wherein a through hole of the implant includes at least one internal thread configured to mate with at least one external thread on the insert sleeve to secure the insert sleeve within the through hole.

* * * * *

UNITED STATES PATENT AND TRADEMARK OFFICE
CERTIFICATE OF CORRECTION

PATENT NO. : 9,642,659 B2
APPLICATION NO. : 14/783598
DATED : May 9, 2017
INVENTOR(S) : Velikov et al.

Page 1 of 1

It is certified that error appears in the above-identified patent and that said Letters Patent is hereby corrected as shown below:

On the Title Page

In item (30), in "Foreign Application Priority Data", in Column 1, Line 1, delete "13163522" and insert --13163522.9-- therefor In the Claims In Column 6, Line 10-11, in Claim 1, delete "direction ," and insert --direction,-- therefor In Column 6, Line 49, in Claim 11, delete "sleeve ," and insert --sleeve,-- therefor Signed and Sealed this
Thirty-first Day of July, 2018

Andrei Iancu
*Director of the United States Patent and Trademark Office*